US006933962B2

(12) United States Patent
Yamamoto (10) Patent No.: US 6,933,962 B2
(45) Date of Patent: Aug. 23, 2005

(54) ELECTRONIC ENDOSCOPE WITH THREE-DIMENSIONAL IMAGE CAPTURING DEVICE

(75) Inventor: Kiyoshi Yamamoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 585 days.

(21) Appl. No.: 10/020,292

(22) Filed: Dec. 18, 2001

(65) Prior Publication Data

US 2002/0082474 A1 Jun. 27, 2002

(30) Foreign Application Priority Data

Dec. 26, 2000 (JP) ..................................... P2000-394229

(51) Int. Cl.[7] ............................................. H04N 13/02
(52) U.S. Cl. ..................... 348/45; 356/3.01; 250/458
(58) Field of Search .............................. 348/45, 65–68; 382/255; 250/458.1; 356/3.01, 5.04, 5.01, 5.03, 5.07–5.08, 613, 477; 600/407, 440, 424, 427, 437

(56) References Cited

U.S. PATENT DOCUMENTS

| | | | | |
|---|---|---|---|---|
| 4,675,529 A | * | 6/1987 | Kushida | 250/458.1 |
| 4,915,498 A | * | 4/1990 | Malek | 356/5.04 |
| 5,081,530 A | | 1/1992 | Medina | |
| 5,434,669 A | * | 7/1995 | Tabata et al. | 356/477 |
| 5,682,895 A | * | 11/1997 | Ishiguro | 600/440 |
| 5,847,832 A | * | 12/1998 | Liskow et al. | 356/613 |
| 6,057,909 A | * | 5/2000 | Yahav et al. | 356/5.04 |
| 6,233,476 B1 | * | 5/2001 | Strommer et al. | 600/424 |
| 6,390,978 B1 | * | 5/2002 | Irion et al. | 600/437 |
| 6,434,416 B1 | * | 8/2002 | Mizoguchi et al. | 600/427 |
| 6,483,948 B1 | * | 11/2002 | Spink et al. | 382/255 |
| 6,778,846 B1 | * | 8/2004 | Martinez et al. | 600/407 |

FOREIGN PATENT DOCUMENTS

| | | |
|---|---|---|
| JP | 4-351074 | 12/1992 |
| JP | 5-211988 | 8/1993 |
| JP | 7-6781 | 1/1995 |
| JP | 7-110381 | 4/1995 |
| WO | 97/01111 | 1/1997 |

OTHER PUBLICATIONS

Article entitled "Design and Development of a Multi–detecting Two–dimensional Ranging Sensor" by S. Christie et al., Measurement Science and Technology, vol. 6, pp. 1301–1308, 1995.

Article entitled "Endoscope Technology", by Shokabo, Popular Science 204, pp. 142–148, with English language translation.

* cited by examiner

*Primary Examiner*—Gims Philippe
(74) *Attorney, Agent, or Firm*—Greenblum & Bernstein, P.L.C.

(57) ABSTRACT

An electronic endoscope comprises a housing and a flexible tube. A light-transmitting optic fiber and a light-receiving optic fiber are provided in the flexible tube. A light source and an imaging device are provided in the housing. The light source outputs a pulsed distance-measuring light beam, which is transmitted along the light-transmitting optic fiber, and irradiated to a subject. A reflected light beam generated by the subject due to the distance-measuring light beam is transmitted along the light-receiving optic fiber, to enter the imaging device, in which an electric charge corresponding to the subject image (i.e., an image signal of a three-dimensional image) is accumulated. A timing of the accumulating operation of the imaging device is delayed depending on the lengths of the fibers.

11 Claims, 5 Drawing Sheets

ELECTRONIC ENDOSCOPE WITH THREE-DIMENSIONAL IMAGE CAPTURING DEVICE

BACKGROUND OF THE INVENTION

1. Field of the Invention

The present invention relates to an electronic endoscope provided with a three-dimensional image capturing device by which a three-dimensional shape of an observed portion in a human body, which is a subject, is sensed.

2. Description of the Related Art

Conventionally, there is known an electronic endoscope of a type described above, which has a pair of light-receiving optic fibers in a flexible tube which is inserted in a human body. Namely, an image of the subject can be detected through the light-receiving optic fibers, and a three-dimensional image of the subject can be captured, using so-called triangulation (see "ENDOSCOPE TECHNOLOGY" ("POPULAR SIENCE 204" issued by Shokabo, pages 142–148)).

In this electronic endoscope, if the distance between the pair of light-receiving optic fibers is short, the stereoscopic quality of the three-dimensional image is reduced, and it is difficult to obtain a three-dimensional image with a high accuracy. Therefore, conventionally, in an electronic endoscope with a three-dimensional image capturing device, it is necessary that the distance between the light-receiving optic fibers is as long as possible. However, this causes the diameter of the flexible tube to become thick.

SUMMARY OF THE INVENTION

Therefore, an object of the present invention is to reduce the diameter of the flexible tube in the electronic endoscope provided with the three-dimensional image capturing device.

According to the present invention, there is provided an electronic endoscope with a three-dimensional image capturing device, comprising a housing, a distance measuring light source, a distance-measurement imaging device, a flexible tube, and a three-dimensional image sensing processor.

The distance measuring light source outputs a distance-measuring light beam, which is a pulsed light beam and which is irradiated on a subject so that a first reflected light beam is generated by the subject. The distance-measurement imaging device receives the first reflected light beam, to accumulate electric charges in accordance with the received amount of the first reflected light beam. The flexible tube is connected to the housing, and has an optic fiber along which at least one of the distance-measuring light beam and the first reflected light beam is transmitted. The three-dimensional image sensing processor controls the accumulating operation of the distance-measurement imaging device, to generate electric charges corresponding to a three-dimensional image of the subject.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention will be described below with reference to the embodiments shown in the drawings.

Figure 1:
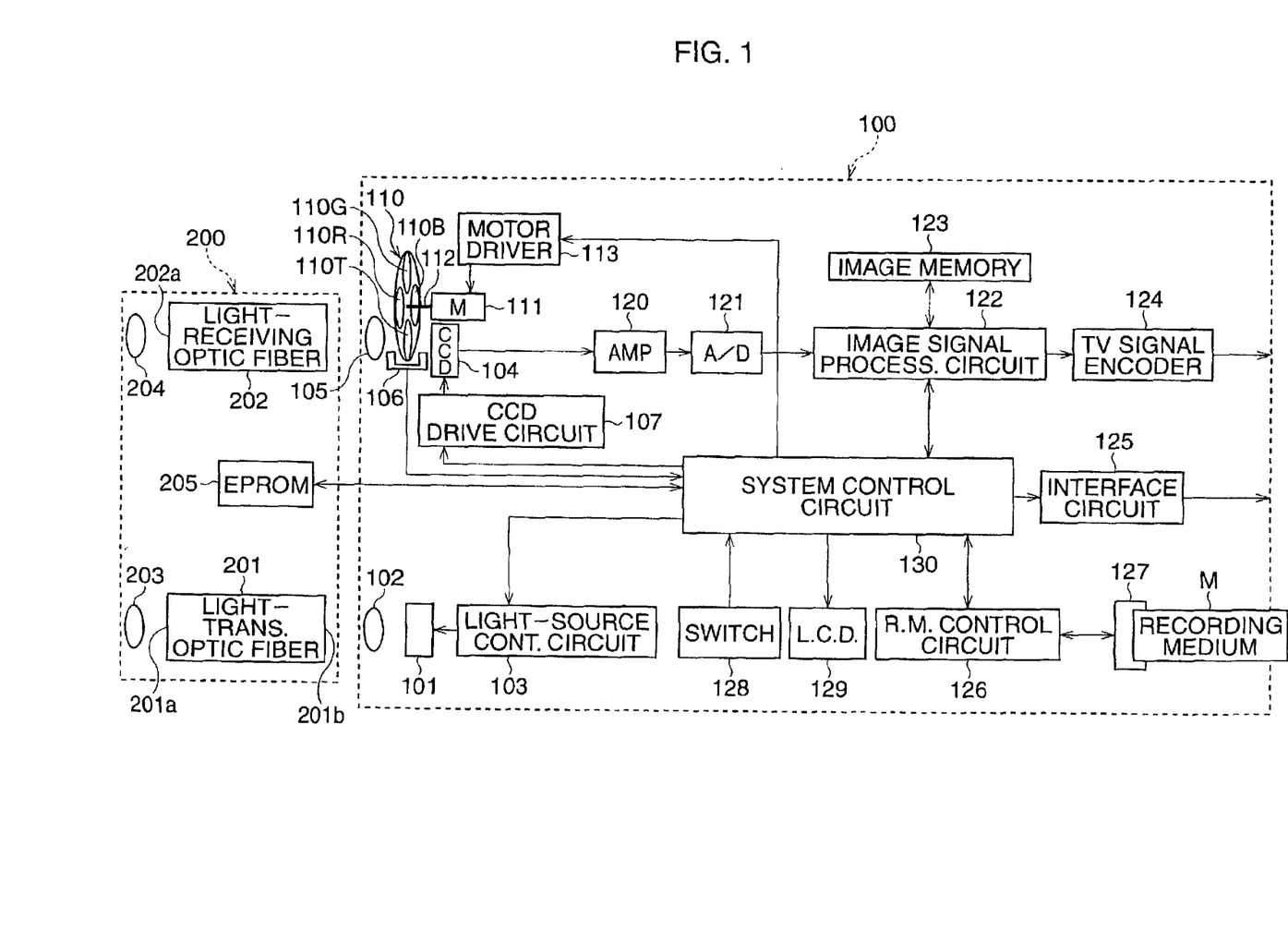
FIG. 1 is a block diagram roughly showing a construction of the inside of an electronic endoscope to which a first embodiment of the present invention is applied.

FIG. 1 shows a general construction of the inside of an electronic endoscope, which is a first embodiment of the present invention.

The electronic endoscope has a housing 100 and a flexible tube 200, which is connected to the housing 100. In the flexible tube 200, a probe, which is inserted into a body, is formed in an elongated slender form and is flexible; the probe is shown as a rectangle in the drawing.

In the flexible tube 200, a light-transmitting optic fiber 201 and a light-receiving optic fiber 202, which have the same length, are housed. The light-transmitting optic fiber 201 transmits a distance-measuring light beam, which is irradiated to a subject or an observed portion in the body. The light-receiving optic fiber 202 transmits a reflected light beam generated by the subject which receives the distance-measuring light beam. A lens 203 is disposed at an end of the flexible tube 200 to face an output end face 201a of the light-transmitting optic fiber 201. A lens 204 is also disposed at the end of the flexible tube 200 to face an incident end face 202a of the light-receiving optic fiber 202. A memory (EPROM) 205 is provided in the flexible tube 200 to store information indicating the lengths of both the light-transmitting optic fiber 201 and the light-receiving optic fiber 202, and other information such as a calibration coefficient used for an imaging process in an image signal processing circuit 122 provided in the housing 100.

A light source 101, provided with a light emitting diode outputting white light, is mounted in the housing 100. The light source 101 irradiates a distance-measuring light beam, which is a pulsed light beam, or continuously irradiates an illuminating light beam. A lens 102 is disposed in front of the light source 101, so that the distance-measuring light beam or the illuminating light beam enters an incident end face 201b of the light-transmitting optic fiber 201 with a high efficiency. The irradiating operation of the light source 101 is controlled by a light-source control circuit 103, which operates in accordance with a command signal output by a system control circuit 130.

An imaging device (CCD) 104 is provided in the housing 100, and aligned on the axis of the light-receiving optic fiber 202. A lens 105 is disposed between an output end face 202b of the light-receiving optic fiber 202 and the CCD 104, to lead light entering through the light-receiving optic fiber 202 to the CCD 104. The CCD 104 is provided with hundreds of thousands of photoelectric conversion elements. A subject image is formed on the CCD 104 through the lens 105, so that the reflected light beam, generated on the subject by the distance-measuring light beam, is received by the photoelectric conversion elements, in which electric charges corresponding to the amount of received light, i.e., the subject image is generated.

A disk-shaped color filter 110 is arranged between the CCD 104 and the lens 105. The central portion of the color filter 110 is connected to an output shaft 112 of a motor 111, so that the color filter 110 is rotated by the motor 111. The rotation control of the motor 111 is performed by a motor driver 113, which is controlled by a command signal output by the system control circuit 130.

In the color filter 110, red(R), green(G), and blue(B) filter element areas 110R, 110G, and 110B, and a transparent area 110T are provided around the central portion. The color filter 110 is controlled in such a manner that one of the areas 110R, 110G, 110B, or 110T is selectively positioned between the CCD 104 and the lens 105. For example, when the R filter element area 110R is positioned between the CCD 104 and the lens 105, an image signal or electric charges corresponding to an R color image is accumulated in the CCD 104.

A position sensor 106 is provided close to the color filter 110, to sense which area of the color filter 110 faces the CCD 104. An output signal from the position sensor 106 is input to the system control circuit 130.

An operation, such as an accumulating operation and a reading operation of electric charges of the CCD 104, is controlled by a CCD drive circuit 107. An electric charge signal, i.e., an image signal read from the CCD 104 is amplified by an amplifier 120, and is converted from an analog signal to a digital signal by an A/D converter 121. The digital image signal is subjected to a process, such as a gamma correction, in the image signal processing circuit 122, and is stored as digital image data in an image memory 123.

The digital image data are read from the image memory 123, and are supplied to a TV signal encoder 124 so that the digital image data can be transmitted to a monitor device (not shown) through a video terminal (not shown). The system control circuit 130 is connected to an interface circuit 125, which in turn is connected to an interface connector (not shown) Therefore, the digital image data read from the image memory 123 are transmitted to a computer (not shown) connected to the interface connector. Further, the system control circuit 130 is connected to an image recording device 127 through a recording medium control circuit 126. Therefore, the digital image data read from the image memory 123 can be recorded in a recording medium M, such as an IC memory card, mounted in the image recording device 127.

A switch group 128, including a release switch, and the liquid crystal display panel 129 are connected to the system control circuit 130.

As described above, the color filter 110 is controlled in such a manner that one of the areas 110R, 110G, 110B, or 110T is selectively positioned between the CCD 104 and the lens 105. When one of the color filter element areas 110R, 110G, or 110B is selected, the light source 101 is controlled to continuously irradiate an illumination light beam, so that an image signal of a two-dimensional image of a color corresponding to the color filter element area is generated in the CCD 104. A sensing operation of the two-dimensional image is omitted, since it is well known.

Conversely, when the transparent area 110T is selected, the light source 101 is controlled to irradiate a pulsed distance-measuring light beam, and thus an image signal of a three-dimensional image indicating a surface shape of the subject is generated in the CCD 104, as will be described later.

Thus, in the first embodiment, the CCD 104 functions as both a distance-measurement imaging device and a two-dimensional image sensing imaging device.

Figure 2:
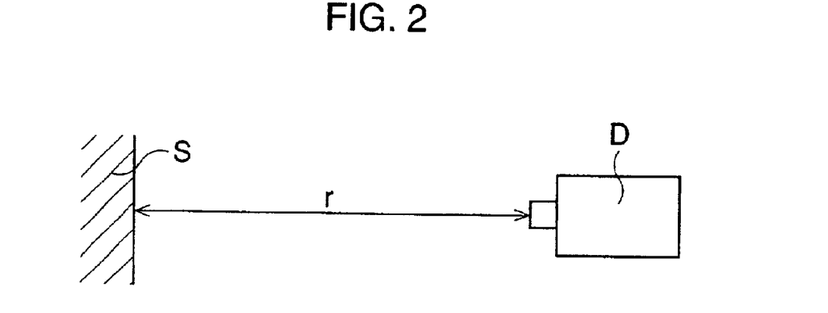
FIG. 2 is a view showing a principle of sensing a three-dimensional image.
Figure 3:
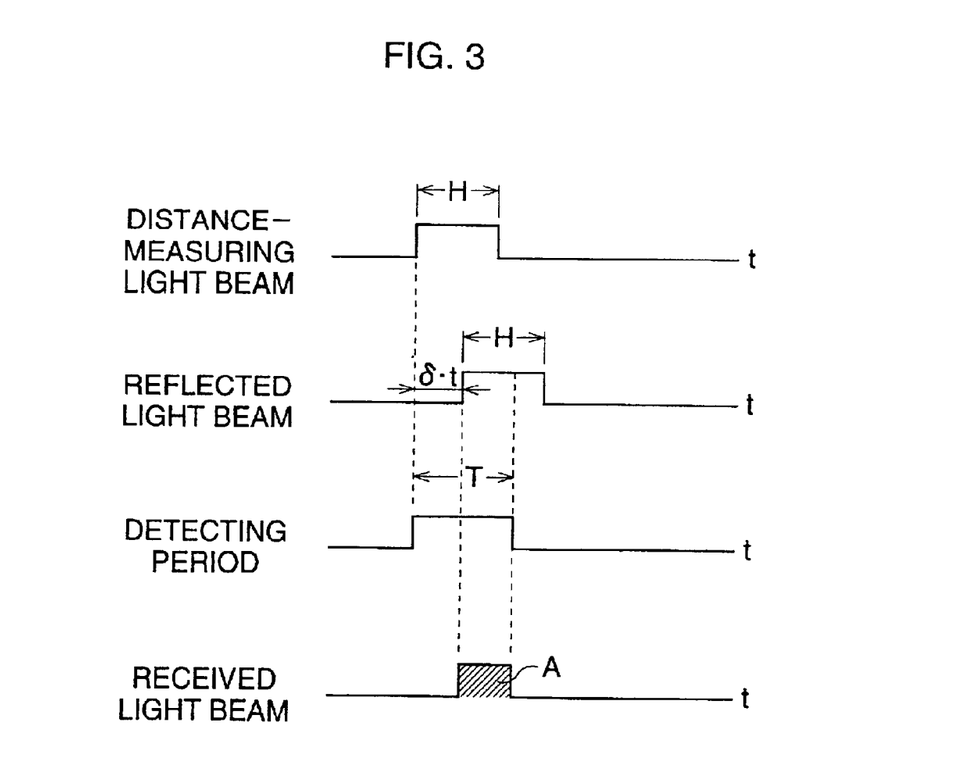
FIG. 3 is a timing chart showing a distance-measuring light beam, a reflected light beam, a detecting period, and the distribution of an amount of light received by a CCD.

With reference to FIGS. 2 and 3, a principle behind a capturing of a three-dimensional image of the subject is described below. Note that, in FIG. 3, the abscissa indicates time "t".

A distance-measuring light beam output by a distance measurement device D is reflected by a subject S, and the reflected light beam is sensed by a CCD (not shown). The distance-measuring light beam is a pulse, the width of which is "H". Accordingly, the reflected light beam is a pulse, the width of which is "H", similar to the distance-measuring light beam. The raise of the pulse of the reflected light beam occurs after the raise of the pulse of the distance-measuring light beam by a time $\delta \cdot t$ ($\delta$ is a delay coefficient). Since the distance-measuring light beam and the reflected light beam have both traveled a distance "r" between the distance measurement device D and the subject S, the distance "r" is represented as follows:

$$r = \delta \cdot t \cdot C / 2$$

wherein "C" is the velocity of light.

For example, by setting a condition in such a manner that the reflected light beam can only be sensed from a raise of the pulse of the distance-measuring light beam to a point prior to a fall of the pulse of the reflected light beam so as to sense a component containing the raise of the pulse of the reflected light beam, i.e., by providing a detecting period T, an amount "A" of received light for the detecting period T becomes a function of the distance "r". Namely, the greater the distance "r" (or the greater the time $\delta \cdot t$), the less the received light amount A.

In this embodiment, by taking advantage of the principle described above, a pixel signal (electric charge) corresponding to the received light amount A is sensed using each of the photoelectric conversion elements of the CCD 104, the distance from the CCD 104 to each point on the surface of the subject S is sensed, and data of the three-dimensional image, which indicates a topography of the subject S, can be obtained concurrently. Further, in the sensing operation of the pixel signal, the pulse of the distance-measuring light beam is repeatedly output with a constant period, so that an electric charge generated in each of the photoelectric conversion elements is integrated. Note that the sensing operation is described in Japanese Unexamined Patent Publication No. 2000-83260 (corresponding to U.S. Ser. No. 09/315, 821), and a correction for an error occurring due to a noise component such as reflectance of the subject surface and ambient light is performed if necessary.

Figure 4:
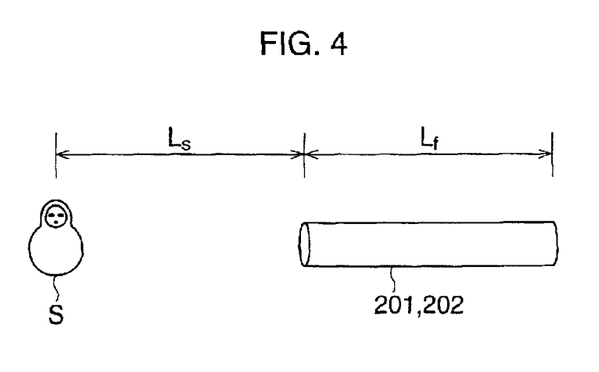
FIG. 4 is a view for explaining a sensing error of a three-dimensional image, which occurs because of the lengths of a light-transmitting optic fiber and a light-receiving optic fiber.
Figure 5:
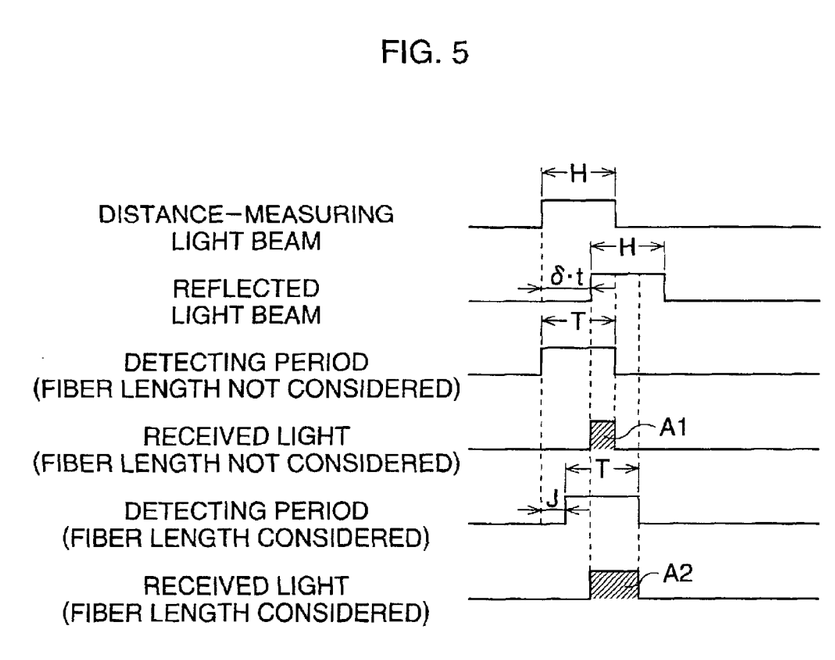
FIG. 5 is a view showing sensing operations of a three-dimensional image, when taking account of the length of a fiber, and without taking account of the length of the fiber.

In the embodiment, as described with reference to FIGS. 4 and 5, a sensing error of the three-dimensional image, which is caused by the lengths of the light-transmitting optic fiber 201 and the light-receiving optic fiber 202 is removed.

It is supposed that the length of each of the fibers 201 and 202 is "Lf", and the distance from the end of each of the fibers 201 and 202 to the subject S is "Ls". The distance, by which the distance-measuring light beam, output from the light source 101 (FIG. 1), reflected by the subject S, and received by the CCD 104 (FIG. 1) proceeds, is equal to the sum of the lengths of the light-transmitting optic fiber 201 and the light-receiving optic fiber 202 (=2×Lf) and the round-trip distance from the front ends of the fibers 201 and 202 to the subject S (=2×Ls). Therefore, the distance-measuring light beam received by the CCD 104 has proceeded further along the lengths of the fibers (=2×Lf) than it does along the distance which is to be sensed. This causes a sensing error for the three-dimensional image. Namely, because of the existence of the fibers 201 and 202, the distance-measuring light beam reaches the CCD 104 with delay of (2×Lf)/C, wherein "C" is the velocity of light.

Accordingly, in the embodiment, an adjusting time "J" is provided so as to remove the sensing error generated by the lengths of the fibers.

$$J=(2\times Lf)/C$$

Namely, when controlling the CCD 104 with the CCD drive circuit 107, the timing of the accumulating operation of electric charge in the photoelectric conversion element is delayed depending on the lengths of the fibers 201 and 202.

Therefore, in comparison with a received light amount A1 (equal to "A" in FIG. 3), sensed using the detecting period in which the length of the fiber is not considered, a received light amount A2, sensed using a detecting period in which the length of the fiber is considered, becomes greater by the amount corresponding to the adjusting time "J". As described above, the received light amount becomes less as the distance to the subject becomes long, and the received light amount A2 has the error (corresponding to the length of the fiber) removed, and is less than the received light amount A1.

As described above, in the embodiment, the light-receiving optic fiber 202 is single, and therefore, in comparison with a device, in which a three-dimensional image of a subject is sensed based on triangulation, using two light-receiving optic fibers, the diameter of the flexible tube 200 can be reduced. Further, since triangulation is not used, i.e., since the length of a baseline used in triangulation is not considered, the distance between the fibers 201 and 202 can be reduced without affecting the accuracy of the distance measurement. Furthermore, in the embodiment, since both the light source 100 and the CCD 104 are housed in the housing 100, the diameter of the flexible tube 200 can be reduced more.

Further, in the embodiment, since the timing of the accumulating operation of the CCD 104 is controlled depending on the lengths of the light-transmitting optic fiber 201 and the light-receiving optic fiber 202, the sensing error of the three-dimensional image, which occurs due to the lengths of the fibers 201 and 202, can be removed, so that the sensing precision can be improved. Further, since information indicating the lengths of the light-transmitting optic fiber 201 and the light-receiving optic fiber 202 is stored in the memory 205, the timing of the accumulating operation of the CCD 104 can be changed in accordance with the length so that the sensing error of the three-dimensional image can be removed, even when the flexible tube 200 is changed.

Note that the CCD 104 can be disposed at the front end of the flexible tube 200. In this case, the adjusting time "J" is calculated as follows, using only the length of the fiber 201:

$$J=Lf/C$$

Figure 6:
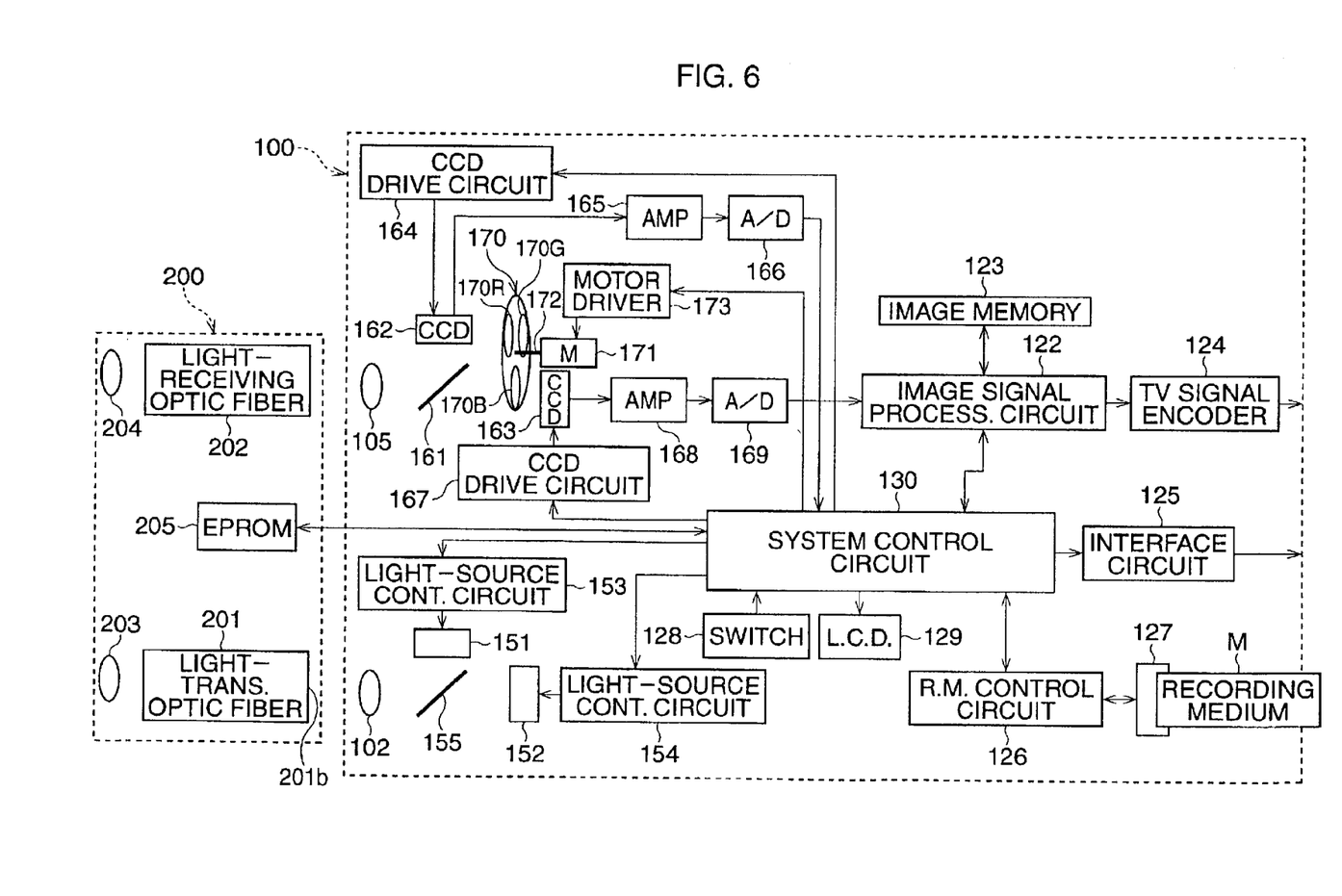
FIG. 6 is a block diagram showing a general construction of the inside of an electronic endoscope to which a second embodiment of the present invention is applied.

FIG. 6 shows a general construction of the inside of an electronic endoscope, which is a second embodiment of the present invention. Parts, different from those of the electronic endoscope of the first embodiment shown in FIG. 1, are described below.

An illuminating light source 152, continuously irradiating an illuminating light beam to a subject, is mounted in the housing 100, in addition to a distance measuring light source 151, outputting a distance-measuring light beam, which is a pulsed light beam and which is irradiated to the subject. The distance measuring light source 151 is provided with an infrared light emitting diode outputting an infrared light beam which is the distance-measuring light beam. An emitting operation of the distance-measuring light source 151 is controlled by a light-source control circuit 153. The illuminating light source 152 is provided with a light-emitting diode outputting a white light beam, and an emitting operation of the illuminating light source 152 is controlled by a light-source control circuit 154. The light-source control circuits 153 and 154 are operated in accordance with a command signal output from the system control circuit 130.

The distance measuring light source 151 and the illuminating light source 152 are disposed so as to face a light-transmitting optic member 155 in such a manner that the axes of the light sources 151 and 152 cross perpendicularly to each other. The lens 102 is provided close to the illuminating light source 152. The light-transmitting optic member 155 reflects the infrared light beam (i.e., the distance-measuring light beam) output from the distance-measuring light source 151 to lead the light beam to the lens 102, and make the white light beam (i.e., the illuminating light beam), output from the illuminating light source 152, pass through to lead the light beam to the lens 102.

The lens 102 faces the incident end face 201b of the light-transmitting optic fiber 201, so that the distance-measuring light beam and the illuminating light beam are transmitted along the light-transmitting optic fiber 201 and irradiated to the subject. The distance-measuring light beam and the illuminating light beam are reflected by the subject, and the reflected light beam enters the light-receiving optic fiber 202. The reflected light beam is then transmitted along the light-receiving optic fiber 202, and enters the lens 105 provided in the housing 100.

A light-receiving optic member 161 is disposed close to the lens 105. A distance-measurement imaging device (CCD) 162 and a two-dimensional image sensing imaging device (CCD) 163 are disposed so as to face the light-receiving optic member 161. The CCD 162 receives the reflected light beam of the distance-measuring light beam, and the CCD 163 receives the reflected light beam of the illuminating light beam. Namely, the light-receiving optic member 161 reflects the infrared light beam (i.e., the reflected light beam of the distance-measuring light beam) to lead the infrared light beam to the CCD 162, and make the white light beam (i.e., the reflected light beam of the illuminating light beam) pass to lead the white light beam to the CCD 163.

The CCD 162 is provided for sensing a three-dimensional image of the subject, similarly to the CCD 104 of the first embodiment. Conversely, the CCD 163 is provided for sensing a two-dimensional image of the subject. A disk-shaped color filter 170 is arranged between the light-receiving optic member 161 and the CCD 163. The central portion of the color filter 170 is connected to an output shaft 172 of a motor 171, so that the color filter 170 is rotated by the motor 171. The rotation control of the motor 171 is performed by a motor driver 173, which is controlled by a command signal output by the system control circuit 130.

The color filter 170 has R, G, and B filter element areas 170R, 170G, and 170B, but the color filter 170 does not have a transparent area, which is different from the color filter 110 (FIG. 1) of the first embodiment. The color filter 170 is controlled in such a manner that one of the areas 170R, 170G, or 170B is selectively positioned between the CCD 163 and the light-receiving optic member 161.

An operation, such as an accumulating operation and a reading operation of electric charges of the CCD 162, is controlled by a CCD drive circuit 164. An image signal read from the CCD 162 is amplified by an amplifier 165, and is converted from an analog signal to a digital signal by an A/D converter 166. Similarly, an operation of the CCD 163 is controlled by a CCD drive circuit 167, and an image signal read from the CCD 163 is amplified by an amplifier 168, and is converted from an analog signal to a digital signal by an A/D converter 169.

Figure 7:
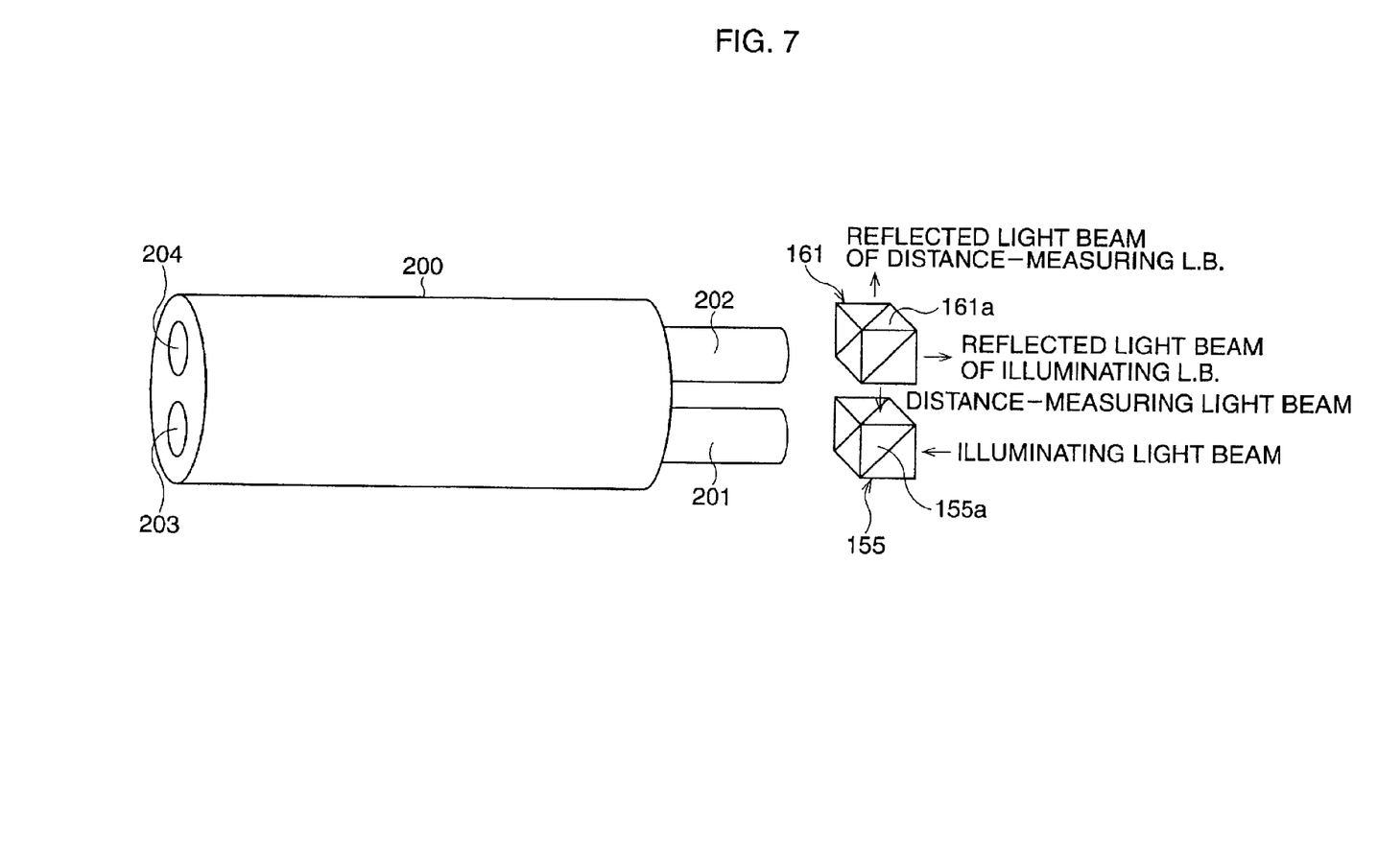
FIG. 7 is a perspective view showing a main structure of the optical system of the electronic endoscope.

FIG. 7 shows a main structure of an optical system of the electronic endoscope, and the distance-measuring light source 151, the illuminating light source 152, the lenses 102 and 105, and the CCDs 162 and 163 are omitted. The light-transmitting optic member 155 and the light-receiving optic member 161 are prisms, in which mirror planes 155a and 161a, reflecting an infrared light beam and passing the other light component, are formed in the prisms.

An operation of the embodiment is described below.

The color filter 170 is controlled in such a manner that the R filter element area 170R, for example, is positioned between the CCD 163 and the lens 105. The distance measuring light source 151 outputs a pulsed distance-measuring light beam (i.e., an infrared light beam), and the illuminating light source 152 continuously outputs an illumination light beam (i.e., a white light beam). The distance-measuring light beam is reflected by the light-transmitting optic member 155, and is led to the light-transmitting optic fiber 201 and irradiated to a subject. The illuminating light beam passes through the light-transmitting optic member 155, and is led to the light-transmitting optic fiber 201 and irradiated to the subject.

The reflected light beam of the distance-measuring light beam, which is generated by the subject, passes through the light-receiving optic fiber 202, and is reflected by the light-receiving optic member 161 to enter the CCD 162. Conversely, the reflected light beam of the illuminating light beam, which is generated by the subject, passes through the light-receiving optic fiber 202, and passes through the light-receiving optic member 161 to enter the CCD 163. In the CCD 162, an image signal of a three-dimensional image of the subject is generated, and in the CCD 163, an R image signal of a two-dimensional image of the subject is generated.

The image signal of the three-dimensional image, input to the system control circuit 130 through the amplifier 165 and the A/D converter 166, is subjected to a predetermined process in the image signal processing circuit 122, and is stored in the image memory 123. The R image signal of the two-dimensional image, input to the image signal processing circuit 122 through the amplifier 168 and the A/D converter 169, is subjected to a predetermined process in the image signal processing circuit 122, and is stored in the image memory 123.

Then, the color filter 170 is controlled in such manner that the G filter element area 170G is positioned between the CCD 163 and the lens 105. Regarding the light sources 151 and 152, the distance-measuring light source 151 is stopped, and only the illuminating light source 152 is actuated. Thus, the illuminating light beam passes through the light-transmitting optic member 155, and reaches the light-transmitting optic fiber 201, by which the illuminating light beam is irradiated to the subject.

The reflected light beam of the illuminating light beam, which is generated by the subject, is led to the CCD 163, as described above. In the CCD 163, a G image signal of the two-dimensional image of the subject is generated. The G image signal is subjected to a predetermined process in the image signal processing circuit 122, and is stored in the image memory 123.

Then, in a similar way as the above, the B filter element area 170B is positioned between the CCD 163 and the lens 105, and only the illuminating light source 152 is actuated so that an illuminating light beam is irradiated to the subject. The reflected light beam of the illuminating light beam, which is generated by the subject, is led to the CCD 163, in which a B image signal is generated. The B image signal is subjected to a predetermined process in the image signal processing circuit 122, and is stored in the image memory 123.

The image signal of the two-dimensional image is read from the image memory 123, and transmitted to a monitor device through the TV encoder 124, for example, so that a color image is indicated by the monitor device. Conversely, the image signal of the three-dimensional image is read from the image memory 123, and transmitted to a computer through the interface circuit 125, for example, so that a three-dimensional image of the subject is indicated on a screen of the display device of the computer. Note that the three-dimensional image is indicated in such a manner that the distance between a point on a surface of the subject and the front end of the flexible tube 200 is converted to a luminance level of the image. For example, the shorter the distance, the brighter the point. The image signals of the two-dimensional image and the three-dimensional image can be recorded in the recording medium M.

As described above, according to the second embodiment, the two-dimensional image and the three-dimensional image can be sensed simultaneously. Therefore, since the user can analyze the data of the three-dimensional image while observing the two-dimensional image, the data analysis can performed more accurately. Further, since the subject, i.e., an observed portion in a human body always stirs or slightly moves, simultaneous sensing is advantage.

The distance-measuring light beam output by the distance measuring light source 151 and the distance-measuring light beam output by the illuminating light source 152 enter the light-transmitting optic fiber 201 through the single optic member 155, and the reflected light beams of the distance-measuring light beam and the illuminating light beam entering the housing 100 through the light-receiving optical fiber 202 are separated by the single optic member 161, and led to the CCDs 162 and 163. Thus, by the provision of the optic members 155 and 161, the portion close to the distance measuring light source 151 and the portion close to the CCDs 162 and 163 can be miniaturized.

Note that, in the second embodiment, the sensing error of the three-dimensional image, which occurs because of the lengths of the light-transmitting optic fiber 201 and the light-receiving optic fiber 202, may be removed in a similar way as the first embodiment.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2000-394229 (filed on Dec. 26, 2000) which is expressly incorporated herein, by reference, in its entirety.

What is claimed is:

1. An electronic endoscope provided with a three-dimensional image capturing device, comprising:
   a housing;
   a distance-measuring light source that outputs a distance-measuring light beam, which is a pulsed light beam and which is irradiated to a subject so that a first reflected light beam is generated by said subject;
   a distance-measurement imaging device that receives said first reflected light beam, to accumulate electric charges in accordance with the received amount of said first reflected light beam;
   a flexible tube that is connected to said housing, and that has an optic fiber along which at least one of said distance-measuring light beam and said first reflected light beam is transmitted; and
   a three-dimensional image sensing processor that controls the accumulating operation of said distance-measurement imaging device in accordance with the length of said fiber, to generate electric charges corresponding to a three-dimensional image of said subject.

2. An electronic endoscope according to claim 1, wherein said distance-measuring light source is provided in said housing.

3. An electronic endoscope according to claim 2, wherein said distance-measurement imaging device is provided in said housing.

4. An electronic endoscope according to claim 1, further comprising an illuminating light source that outputs an illuminating light beam, and a light-transmitting optical element that leads said distance-measuring light beam and said illuminating light beam to said optic fiber, said distance-measuring light source and said illuminating light source being disposed so as to face said light-transmitting optical element.

5. An electronic endoscope according to claim 4, further comprising a light-receiving optical element disposed in such a manner that said first reflected light beam, output from said optic fiber, enters said light-receiving optical element, said distance-measurement imaging device, and a two-dimensional image-sensing imaging device being disposed so as to face said light-receiving optical element.

6. An electronic endoscope according to claim 1, wherein said three-dimensional image sensing processor controls the accumulating operation in such a manner that a timing of the accumulating operation is delayed depending on the length of said optic fiber.

7. An electronic endoscope according to claim 1, further comprising an illuminating light source that continuously irradiates an illuminating light beam to said subject so that a second reflected light beam is generated by said subject, and a two-dimensional image-sensing imaging device that receives said second reflected light beam, to sense a two-dimensional image of said subject.

8. An electronic endoscope according to claim 7, wherein said illuminating light source is provided in said housing.

9. An electronic endoscope according to claim 7, wherein said two-dimensional image-sensing imaging device is provided in said housing.

10. An electronic endoscope according to claim 7, wherein said optic fiber comprises a light-transmitting optic fiber that irradiates said distance-measuring light beam and/or said illuminating light beam on said subject, and a light-receiving optic fiber that receives said reflected light beam generated by said subject.

11. An electronic endoscope according to claim 10, wherein said flexible tube is provided with a memory in which information indicating the length of each of said light-transmitting optic fiber and said light-receiving optic fiber is stored.

* * * * *